US007815597B2

(12) United States Patent
Stypulkowski

(10) Patent No.: US 7,815,597 B2
(45) Date of Patent: Oct. 19, 2010

(54) SYSTEM AND METHOD OF TREATING STUTTERING BY NEUROMODULATION

(75) Inventor: Paul H. Stypulkowski, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 560 days.

(21) Appl. No.: 11/168,604

(22) Filed: Jun. 27, 2005

(65) Prior Publication Data

US 2006/0041221 A1     Feb. 23, 2006

Related U.S. Application Data

(62) Division of application No. 10/001,751, filed on Oct. 31, 2001, now Pat. No. 6,944,497.

(51) Int. Cl.
   *A61M 31/00*     (2006.01)
   *A61F 5/58*     (2006.01)
   *A61N 1/34*     (2006.01)
   *A61B 5/04*     (2006.01)

(52) U.S. Cl. .................. 604/67; 604/890.1; 604/891.1; 604/500; 600/23; 600/544; 600/546; 607/45; 607/48; 607/118

(58) Field of Classification Search .............. 604/890.1, 604/891.1, 93.01, 528, 502–503, 66, 43, 604/500, 67; 607/48, 118, 45; 128/899; 600/23, 544, 546
See application file for complete search history.

(56) References Cited

U.S. PATENT DOCUMENTS

| | | | |
|---|---|---|---|
| 3,566,858 A | 3/1971 | Larson | |
| 4,020,567 A | 5/1977 | Webster | |
| 4,662,847 A | 5/1987 | Blum | |
| 4,685,448 A * | 8/1987 | Shames et al. | ................. 600/23 |
| 4,692,147 A * | 9/1987 | Duggan | .................... 604/891.1 |
| 4,784,115 A * | 11/1988 | Webster | ....................... 600/24 |

(Continued)

FOREIGN PATENT DOCUMENTS

WO     WO99/40572     8/1999

OTHER PUBLICATIONS

Kiziltan, G., et.al. "Stuttering may be a type of actioin dystonia." Movement Disorders. vol. 11, No. 3, 1996. pp. 278-282.*

(Continued)

*Primary Examiner*—Nicholas D Lucchesi
*Assistant Examiner*—Quynh-Nhu H Vu
(74) *Attorney, Agent, or Firm*—Stephen W. Bauer; Beth L. McMahon

(57) ABSTRACT

Stuttering-treatment techniques using neural stimulation and/or drug delivery. One or more electrodes and/or a catheter are implanted adjacent to sites in the brain. A signal generator and the electrode deliver stimulation to a first site. A pump and the catheter deliver one or more therapeutic drugs to a second site. The first and second sites could be: the supplementary motor area, the centromedian circuit, the dorsomedial nuclei, the lateral prefrontal circuit, or other paramedian thalamic and midbrain nuclei. The stuttering treatment could be performed via periodic transcranial magnetic stimulation. A sensor, located near the patient's vocal folds, can be used for generating a signal responsive to activity of the patient's speech-producing muscles. A controller adjusts one or more stimulation parameters in response to the signal from the sensor.

28 Claims, 12 Drawing Sheets

U.S. PATENT DOCUMENTS

| | | | |
|---|---|---|---|
| 4,909,261 A | | 3/1990 | Rothenberg |
| 5,111,814 A | * | 5/1992 | Goldfarb ..................... 607/48 |
| 5,113,859 A | * | 5/1992 | Funke ........................... 607/4 |
| 5,259,387 A | | 11/1993 | de Pinto |
| 5,478,304 A | * | 12/1995 | Webster ....................... 600/23 |
| 5,735,814 A | * | 4/1998 | Elsberry et al. ............... 604/43 |
| 5,765,135 A | * | 6/1998 | Friedman et al. ............ 704/276 |
| 5,794,203 A | * | 8/1998 | Kehoe ......................... 704/271 |
| 5,843,142 A | | 12/1998 | Sultan |
| 5,940,798 A | | 8/1999 | Houde |
| 5,961,443 A | | 10/1999 | Rastatter et al. |
| 6,094,598 A | * | 7/2000 | Elsberry et al. ............. 607/116 |
| 6,128,538 A | * | 10/2000 | Fischell et al. ................ 607/45 |
| 6,227,203 B1 | * | 5/2001 | Rise et al. ................... 128/898 |
| 6,231,500 B1 | * | 5/2001 | Kehoe ......................... 600/23 |
| 6,381,496 B1 | * | 4/2002 | Meadows et al. ............. 607/59 |
| 6,944,497 B2 | * | 9/2005 | Stypulkowski ................. 607/2 |
| 2002/0042632 A1 | * | 4/2002 | Iaizzo et al. .................. 607/27 |
| 2006/0041242 A1 | * | 2/2006 | Stypulkowski ............. 604/503 |

OTHER PUBLICATIONS

G. Kiziltan et al., "Stuttering may be a type of action dystonia", Movement disorder, vol. 11, No. 3, 1996, pp. 278-282.*

Kazuo, Abe et al., Repetitive Speech Disorder Resulting from Infarcts in the Paramedian Thalami and Midbrain, Journal of Neurology, Neurosurgery and Psychiatry, 1993, 56: 1024.

Orlando, J. Andy et al., Stuttering Acquired from Subcortical Pathologies and Its Alleviation from Thalamic Perturbation, Brain and Language, 1992, 42:385-401, Academic Press.

Subhash, C. Bhatnager et al., The Effect of Thalamic Stimulation in Processing of Verbal Stimuli in Dichotic Listening Tasks, a Case Study, Brain and Language, 1989, 36:236-2.

Subhash C. Bhatnagar et al., Alleviation of Acquired Stuttering with Human Centremedlan Thalamic Stimulation, Journal of Neurology, Neurosurgery and Psychiatry, 1989, 52:1182.

Orlando, J. Andy, et al., Thalamic-Induced Stuttering (Surgical Observation), Journal of Speech and Hearing Research, Aug. 1991, 796-800, vol. 34, American Speech-Language.

Murio, A., et al. Cessation of Stuttering after Bilateral Thalamic Infarcation, www.neurology.org, 1999, 4 pages.

Nagafuchi, Masaaki et al., Speech Disorder Due to Damage of the Left Premotor Area, 1989, 328-333.

* cited by examiner

SYSTEM AND METHOD OF TREATING STUTTERING BY NEUROMODULATION

RELATED APPLICATIONS

This application is a Divisional application of U.S. application Ser. No. 10/001,751, filed Oct. 31, 2001. The entire content of this U.S. application is incorporated herein by reference.

FIELD OF THE INVENTION

The invention relates to therapeutic treatment of stuttering. More particularly, the invention relates to treating stuttering via neural stimulation and drug therapy techniques.

BACKGROUND OF THE INVENTION

Stuttering is a speech-disfluency problem that can have significant developmental and social impacts upon stuttering individuals. Stuttering can include repetitions of parts of words and/or whole words, prolongation of sounds, interjections of sounds or words, and unduly prolonged pauses.

Conventional stuttering treatment techniques typically focus on alerting the patient that stuttering is occurring and having the patient try to modify their breathing and/or speech patterns in an attempt to avoid stuttering. For instance, U.S. Pat. No. 4,020,567, entitled Method and Stuttering Therapy Apparatus, issued to Webster on May 3, 1977, discloses a system for helping individuals determine when they are stuttering. The system generates an electrical signal based on the person's speech and uses the signal to detect certain speech characteristics corresponding to stuttering. A first embodiment detects speech onset errors during the first 100 milliseconds of syllable pronunciation. In a second embodiment, stuttering is detected by evaluating the rate of change in the amplitude of the person's speech. An LED is illuminated to notify a system-user that stuttering is occurring. The system disclosed by Webster is intended for use by stutterers while they practice learning not to stutter.

U.S. Pat. No. 4,662,847, entitled Electronic Device and Method for the Treatment of Stuttering, issued to Blum on May 5, 1987, discloses an electronic device for treating stuttering. The device transmits electronic speech signals from a microphone to an earphone through two paths. One path is synchronous. The other path is asynchronous. During normal speech, the synchronous speech signal is transmitted to the earphone. At any pause in phonation, the device switches to the asynchronous path and transmits speech in a delayed auditory feedback mode until a change in the user's speech occurs.

U.S. Pat. No. 4,784,115, entitled Anti-Stuttering Device and Method, issued to Webster on Nov. 15, 1988, discloses an anti-stuttering device for enhancing speech fluency. The device detects vocal pulses generated by the opening and closing of a speaker's vocal folds. Electrical signals representative of the vocal pulses are transmitted to a receiver in the speaker's sealed ear canal where these signals are reproduced as audio pulses. The device reduces stuttering by providing an early indication of the characteristics of the speaker's voice via audio pulses. The audio pulses produce a resonant effect within the person's ear canal.

U.S. Pat. No. 5,794,203, entitled Biofeedback System for Speech Disorders, issued to Kehoe on Aug. 11, 1988, discloses a biofeedback system for speech disorders that detects disfluent speech and provides auditory feedback to enable fluent speech. The disfluent-speech detector can be either an electromyograph (EMG) or an electroglottograph (EGG). EMG is a system that measures the electrical activities of muscles through electrodes attached to a person's body. EGG records the opening and closing of a person's vocal folds. EGG's use two electrodes on a person's neck and measure the resistance between the electrodes. This resistance changes as the vocal folds open and close. An EGG can show the frequency of the vocal folds. This is the fundamental pitch of the user's voice, without the harmonics produced by the nasal cavities, mouth, and the like.

The system disclosed by Kehoe includes an electronic controller connected to an EMG and frequency-altered auditory feedback (FAF) circuit. The controller receives data from the EMG regarding muscle tension in the user's vocal cords, masseter, and/or other speech-production muscles. The controller then controls the pitch of the FAF circuit in accordance with the user's muscle tension. The user wears a headset with a microphone and headphones. Three EMG electrodes are taped onto the user's neck and/or jaw. When the user speaks fluently, with speech-production muscles relaxed, the user's hears his or her voice shifted lower in pitch. This downward-shifted pitch is relaxing and pleasant, sort of like hearing James Earl Jones speak. If the user's speech-production muscles are abnormally tense, however, the user will hear his or her voice shifted higher in pitch.

U.S. Pat. No. 6,231,500, entitled Electronic Anti-Stuttering Device Providing Auditory Feedback and Disfluency-Detecting Biofeedback, issued to Kehoe on May 15, 2001, is a continuation-in-part of U.S. Pat. No. 5,794,203. The Kehoe '500 patent discloses micropower impulse radar (MIR) as an alternative to EMG biofeedback for monitoring a user's muscle activity to detect disfluency. MIR is short-range radar, using commonly available microchips. Unlike other radar, MIR is small and inexpensive. A small sensor for monitoring laryngeal activity could be taped to a user's throat.

Conventional treatment techniques for treating stuttering typically do not use neurostimulation and/or drug delivery devices. These types of devices, however, are capable of treating a number of neurological disorders as well as symptoms of those disorders. In the context of neurostimulators, an electrical lead having one or more electrodes is typically implanted near a specific site in the brain of a patient. The lead is coupled to a signal generator that delivers electrical energy through the electrodes and creates an electrical field causing excitation of the nearby neurons to directly or indirectly treat the neurological disorder or symptoms of the disorder. In the context of a drug delivery system, a catheter coupled to a pump is implanted near a treatment site in the brain. Therapeutics are delivered to the treatment sites in predetermined dosages through the catheter.

In an article entitled Cessation of Stuttering After Bilateral Thalamic Infarction, A. Muroi et al. describe their observation of a patient who, after paramedian thalamic infarction, experienced cessation of stuttering. *Neurology*, vol. 53, pp. 890-91 (September (1 of 2) 1999. In this article, A. Muroi et al. state that neuroimaging studies indicate that the occlusion of a single artery, the mesencephalic artery, have given rise to the infarction in the bilateral medial thalamus and rostral mesencephalic tegmentum. Further, in developmental stuttering, regional cerebral blood flow (rCBF) was observed as relatively increased in the medial and lateral prefrontal areas and in the orbital cortices, and also in the supplementary motor area (SMA) and the superior lateral premotor cortex. A. Muroi et al. then discuss a study by Nagafuchi and Takahashi in which a patient started to stutter after an infarct in the SMA. Another article, by Abe et al., describes a case of stuttering-like repetitive speech disorder after paramedian thalamomesencephalic infarction. Yet another article, by Andy and Bhatnager, reported that stuttering was elicited by destruction of the centromedian (CM) in one case; they also found that stimulation of the same region alleviated the acquired stuttering in another case. The work reported by Andy and Bhatnagar related only to adult onset, acquired stuttering, due to the presence of cortical or subcortical pathologies (related to a central pain syndrome), but did not involve the more common form of developmental stuttering. Further, there is no teaching in their work on the application of DBS or drug delivery for the chronic treatment of developmental stuttering as a disorder of the motor system. The dorsomedial (DM) nuclei and CM, which were involved in the case reported by A. Muroi et al., are reciprocally connected to the lateral prefrontal area and SMA, respectively. In light of these studies and the case reported by A. Muroi et al., the A. Muroi et al. article speculates that disordered function of the SMA-CM circuit or DM-lateral prefrontal cortex is responsible for developmental and acquired stuttering. Therefore, it may be possible to treat either developmental or acquired stuttering by stimulation or drug delivery of the neural circuits involved in stuttering.

Based on the foregoing, there is a need for stuttering-treatment techniques that use neural stimulation and/or drug delivery to target the neurological underpinnings of stuttering.

BRIEF SUMMARY OF THE INVENTION

The invention is directed toward various stuttering-treatment techniques using neural stimulation and/or drug delivery. In accordance with various inventive principles, a catheter is coupled to an implantable pump for infusing therapeutic dosages of at least one drug. At least one implantable electrode is coupled to a signal generator for delivering electrical stimulation. The invention may include various permutations and/or combinations of the following steps: implanting the one or more electrodes adjacent to a first predetermined site in the brain; implanting the catheter so that the discharge portion lies adjacent to a second predetermined site in the brain; coupling the proximal end of the implanted electrode to the signal generator; coupling the catheter to the pump; and operating the signal generator and the pump to stimulate or inhibit neurons of the first and second sites in the brain by delivering electrical stimulation to the first site and by delivering one or more drugs to the second predetermined site. The first and/or second predetermined sites can be: the supplementary motor area, the perisylvian speech-language cortex, the centromedian circuit, the dorsomedial nuclei, the lateral prefrontal circuit, the mesothalamic reticular formation, the basal ganglia, or other paramedian thalamic and midbrain nuclei and fiber tracts including, but not limited to the red nucleus, the habenulointerpeduncular tract, the prerubral area, the zona incerta, the thalamic primary sensory relay nuclei (e.g., ventrooral nucleus, ventrolateral nucleus), the parafasicular nucleus, and the intralaminar nucleus.

In accordance with the invention, the stuttering treatment may be performed via periodic, such as once per week, transcranial magnetic stimulation of a predetermined site of a patient's brain for a predetermined duration, such as 30 minutes. The transcranial-magnetic-stimulation site is delivered to: the supplementary motor area, the perisylvian speech-language cortex, the centromedian circuit, the dorsomedial nuclei, the lateral prefrontal circuit, the mesothalamic reticular formation, the basal ganglia, or other paramedian thalamic and midbrain nuclei and fiber tracts including, but not limited to the red nucleus, the habenulointerpeduncular tract, the prerubral area, the zona incerta, the thalamic primary sensory relay nuclei (e.g., ventrooral nucleus, ventrolateral nucleus), the parafasicular nucleus, and the intralaminar nucleus.

A system, in accordance with the invention, for therapeutically treating stuttering in a patient is disclosed. The system includes: a signal generator; at least one implantable lead, coupled to the signal generator, for delivering electrical stimulation to at least one predetermined site of the patient's brain; a sensor, located near the patient's vocal folds, for generating a signal responsive to activity of the patient's vocal folds; a controller that adjusts at least one stimulation parameter in response to the signal from the sensor. The controller could detect when the patient starts speaking and then start the electrical stimulation in response to that patient having started to speak. The controller could then stop the electrical stimulation a predetermined amount of time after the patient started speaking. The sensor could be an electromyographic sensor, an electroglottographic sensor, or a microphone, which could be implanted within the patient's body. The controller could use a speech-recognition algorithm for detecting stuttering based on the signal received from the sensor.

In one example embodiment, the system comprises a sensor for generating a signal indicative of activity of the patient's speech-producing muscles and a controller that performs speech-recognition processing on the signal from the sensor to detect stuttering and that adjusts at least one stimulation parameter of the electrical stimulation in response to detecting stuttering. According to another aspect, the controller may detect when the patient starts speaking and starts the electrical stimulation in response to detecting that the patient has started to speak. In one example embodiment, the sensor generates a signal responsive to activity of the patient's speech-producing muscles and the controller includes a speech-recognition module for performing speech-recognition processing on the signal from the sensor to detect stuttering and that adjusts at least one stimulation parameter in response to detecting stuttering.

Other advantages, novel features, and further scope of applicability of the invention will be set forth in the following detailed description.

DETAILED DESCRIPTION OF THE INVENTION

Figure 1:
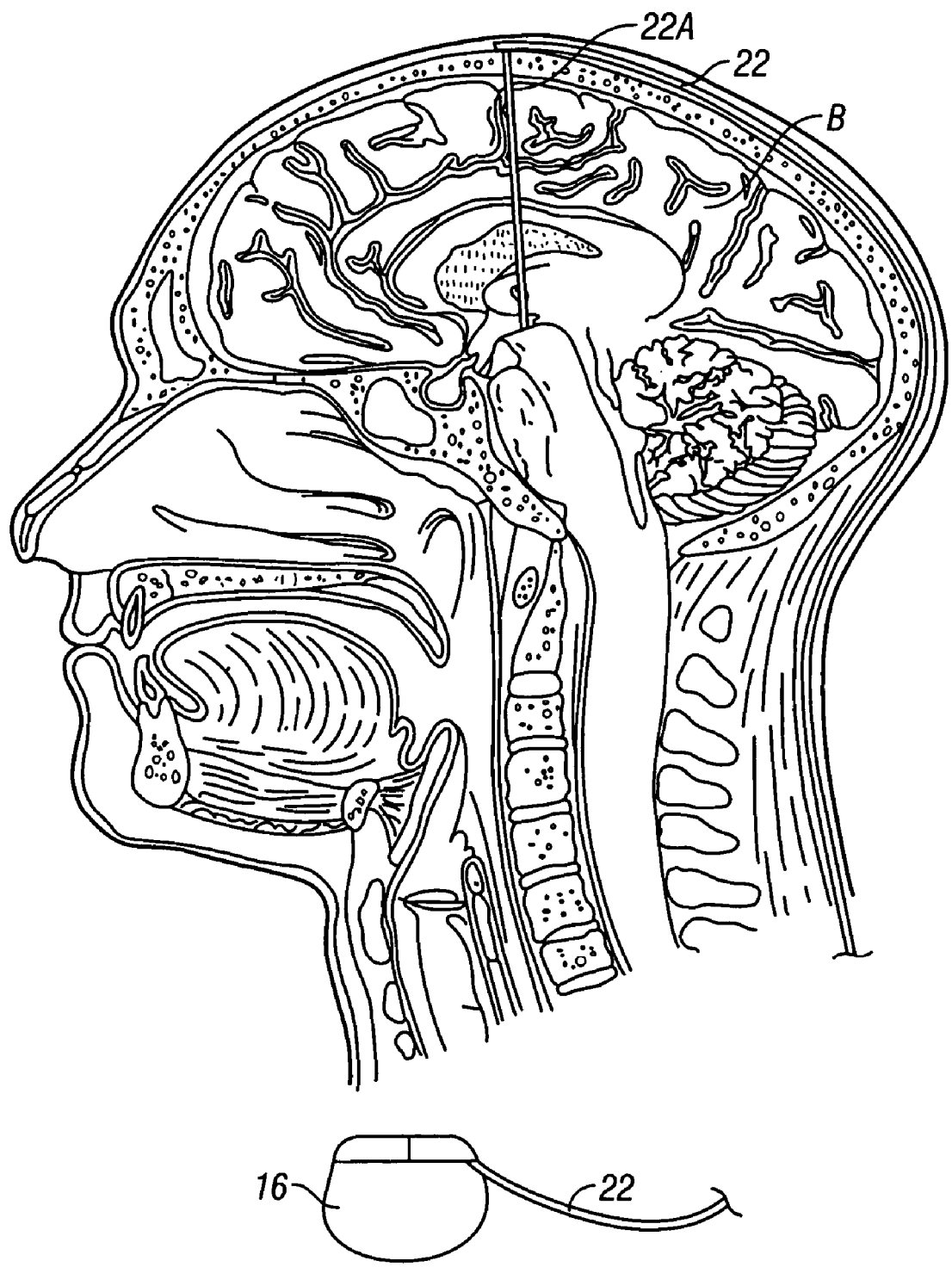
FIG. 1 is a diagrammatic illustration of a system for treating stuttering illustrating a signal generator connected to an electrode implanted in a patient's brain.

The neurogenic basis of stuttering is not well understood, but an analogy can be drawn between stuttering and motor tremor in a person's extremities or axial musculature. It is know that in some forms of tremor the occurrence of abnormal neural activity in specific brain regions (e.g., thalamus) is associated with the presence of tremor. It is also known that treatment of these regions with electrical stimulation or drug delivery can reduce or abolish tremor. The structures that are apparently involved in stuttering are the supplementary motor area, (SMA), the centromedian circuit (CM circuit), the dorsomedial nuclei (DM nuclei), the lateral prefrontal circuit, and other paramedian thalamic and midbrain nuclei, and by analogy to tremor, it is hypothesized that abnormal neural activity in these structures and circuits is associated with the presence of stuttering.

The thalamus and cortex are connected by a network of parallel neural circuits that send information in both directions to ultimately control thoughts, emotions, motor behaviors, and various other higher level functions. Each of the various types of functions appears to have discrete anatomical circuit associated with them. If abnormal patterns of neural activity (e.g., too much or too little activity) arise in a specific circuit due to disease, trauma, or developmental causes, the result is often a clinical symptom associated with the specific functional area. For instance, obsessive-compulsive disorder is thought to be due to hyperactivity in the loop connecting orbital-frontal cortex with the medial thalamus. Tremor in a specific body region appears to arise due to over activity in the loop between the basal ganglia, thalamus and the motor cortex subserving that body part. Similarly, stuttering may be related to abnormal activity in the basal ganglia and thalamo-cortical loops that control the production of speech.

It has been hypothesized that two such loops are involved in language production and therefore in the dysfunction of stuttering: an "outer" linguistic loop, which controls the selection of speech information, and an "inner" motor loop that controls the actual production of speech sounds via control of the vocal apparatus. The linguistic loop appears to be mediated by neural circuits in the perisylvian speech-language cortex, and the motor loop by cortico-striatal-thalamo-cortical circuits. A disruption in timing between these circuits has been suggested as a possible mechanism of stuttering. By applying electrical stimulation and or drug delivery within these circuits, it may be possible to re-establish the proper timing relationships and thereby reduce or eliminate stuttering.

For example, the supplementary motor area (SMA), part of the motor loop, can be thought of as generating a signal indicative of the intention to do something, such as begin speaking. That signal then gets passed to the motor cortex, which is a part of the brain that sends a corresponding signal to a person's muscles, including a person's vocal cords, to do something, such as making speech sounds.

Disruption of the appropriate precursor signal from the SMA may be responsible for a stutterer's inability to speak fluently when they are starting to say something. Such a disruption may also be responsible for a stutterer's inability to break out of a loop in which the same sound is being unintentionally repeated and the inability to progress to the next stage of speaking, which occurs in fluent speech.

This invention includes treatment techniques for ameliorating stuttering by influencing levels of activity in various neuronal loops associated with stuttering. These techniques include drug delivery, electrical and magnetic stimulation, and/or closed loop feedback systems for detecting the occurrence of speech or stuttering.

FIG. 1 is a diagrammatic illustration of a patient with an implant of a neurostimulation system employing an embodiment of the present invention. An implantable signal generator 16 produces stimulation signals to various predetermined sites within a patient's brain, B. The predetermined sites may include the supplementary motor area (SMA), the perisylvian speech-language cortex, the centromedian circuit (CM circuit), the dorsomedial nuclei (DM nuclei), the lateral prefrontal circuit, the mesothalamic reticular formation, the basal ganglia and other paramedian thalamic and midbrain nuclei and fiber tracts including, but not limited to the red nucleus, the habenulointerpeduncular tract, the prerubral area, the zona incerta, the thalamic primary sensory relay nuclei (e.g., ventrooral nucleus, ventrolateral nucleus), the parafasicular nucleus, and the intralaminar nucleus. Device 16 may take the form of a signal generator such as model 7424 manufactured by Medtronic Inc. under the trademark Itrel II®.

As depicted in FIG. 1, a conductor 22 is implanted below the skin of a patient. The distal end of conductor 22 terminates in a lead 22A. Lead 22A may take the form of any of the leads sold with Medtronic's Model 7424 signal generator for stimulation of the brain. The proximal end of conductor 22 is coupled to signal generator 16.

The distal end of lead 22A terminates in a stimulation electrode located at a predetermined area of the brain, B. The distal end of lead 22A is implanted using stereotactic techniques that are well known by those skilled in the art. The physician determines the number of electrodes needed for the particular treatment.

Figure 2:
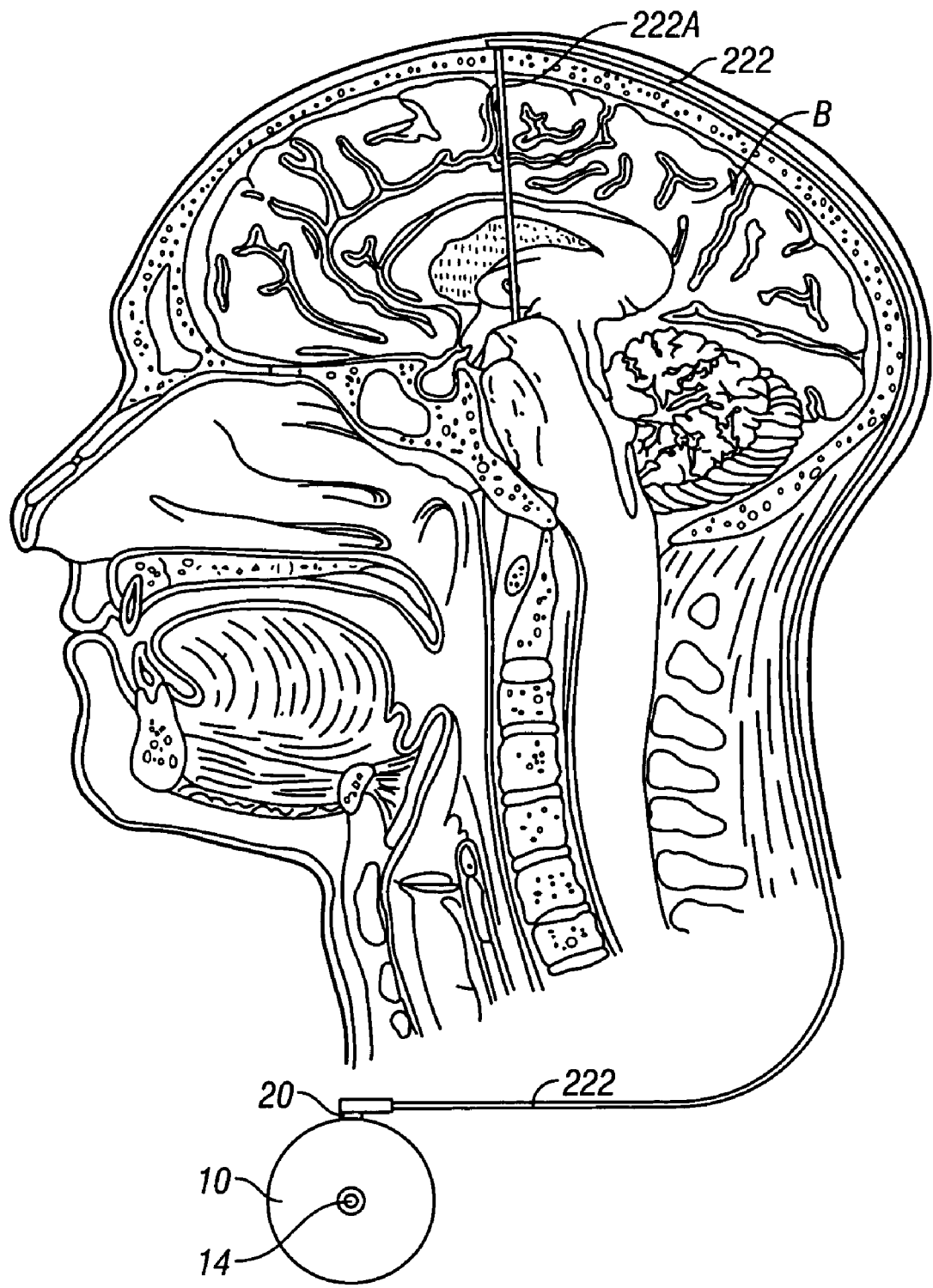
FIG. 2 is a diagrammatic illustration of a stuttering-treatment system including an implantable pump and catheter for delivering therapeutics to predetermined sites in a patient's brain.

FIG. 2 is a diagrammatic illustration of a patient having an implant of a drug delivery system employing an embodiment of the present invention. The system distributes a therapeutic agent to predetermined sites in the brain selected by a physician. The system uses a pump 10 that can be an implantable pump like the Medtronic SynchroMed® pump or an external pump. As depicted in FIG. 2, the pump 10 has a port 14 into which a hypodermic needle can be inserted to inject therapeutic to fill the pump 10. In the system shown, the therapeutic is delivered from pump 10 through a catheter port 20 into a catheter 222. Catheter 222 may be implanted below the skin of a patient using well-known stereotactic placement techniques and positioned to deliver the therapeutic to the predetermined sites within the brain, B. The predetermined sites may include the supplementary motor area (SMA), the perisylvian speech-language cortex, the centromedian circuit (CM circuit), the dorsomedial nuclei (DM nuclei), the lateral prefrontal circuit, the mesothalamic reticular formation, the basal ganglia and other paramedian thalamic and midbrain nuclei and fiber tracts including, but not limited to the red nucleus, the habenulointerpeduncular tract, the prerubral area, the zona incerta, the thalamic primary sensory relay nuclei (e.g., ventrooral nucleus, ventrolateral nucleus), the parafasicular nucleus, and the intralaminar nucleus.

Figure 3:
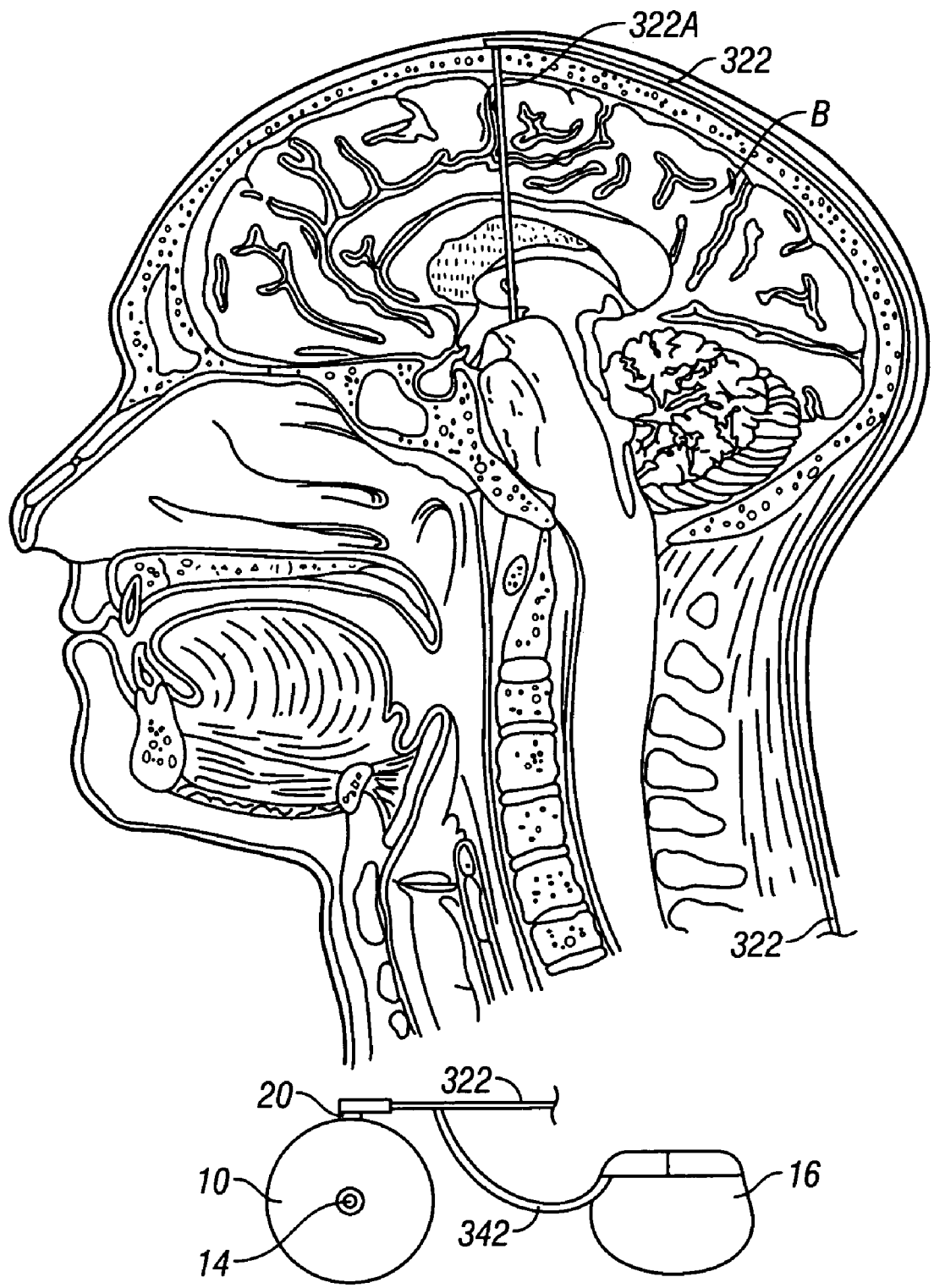
FIG. 3 is a diagrammatic illustration of a stuttering-treatment system including a combined catheter and electrode implanted in a patient's brain.

FIG. 3 is a diagrammatic illustration of a patient having an implant of a neurological system employing an embodiment of the present invention. The system as shown in FIG. 3, illustrates a combined catheter electrode, 322, that can distribute both stimulation signals and therapeutics from the signal generator 16 and pump 10, respectively.

The combined catheter electrode 322 terminates with a cylindrical hollow tube 322A having a distal end implanted into a predetermined location of a patient's brain, B. The distal end of tube 322A is implanted using stereotactic techniques well known by those skilled in the art. Tube 322A includes an outer cylindrical insulation jacket (not shown) and an inner insulation jacket (not shown) that defines a cylindrical catheter lumen. A multifular coil of wire, multiflar stranded wire or flexible printed circuit is embedded in tube 322A (not shown).

Trans-cranial magnetic stimulation could also be used as a means to deliver therapeutic stimulation to the nervous system to treat stuttering. This magnetic stimulation would tend to be more of a clinical application as opposed to a portable and/or human-implantable device. In accordance with the invention, a patient's stuttering could be treated periodically, such as once per week, via trans-cranial magnetic stimulation of the supplementary motor area, (SMA), the centromedian circuit (CM circuit), the dorsomedial nuclei (DM nuclei), the lateral prefrontal circuit, and other paramedian thalamic and midbrain nuclei and fiber tracts including, but not limited to the red nucleus, the habenulointerpeduncular tract, the prerubral area, the zona incerta, the thalamic primary sensory relay nuclei (e.g., ventrooral nucleus, ventrolateral nucleus), the parafasicular nucleus, and the intralaminar nucleus. The Magpro stimulator available from Medtronic, Inc. of Minneapolis Minn. is an example of a suitable magnetic stimulator. Magnetic stimulators of this type are capable of causing electrical current flow in particular regions of a patient's brain thereby activating specific neural structures or circuits. Such magnetic stimulation has been used clinically as a diagnostic tool to evaluate the condition of the motor system, and therapeutically to treat disorders such as depression.

Figure 4:
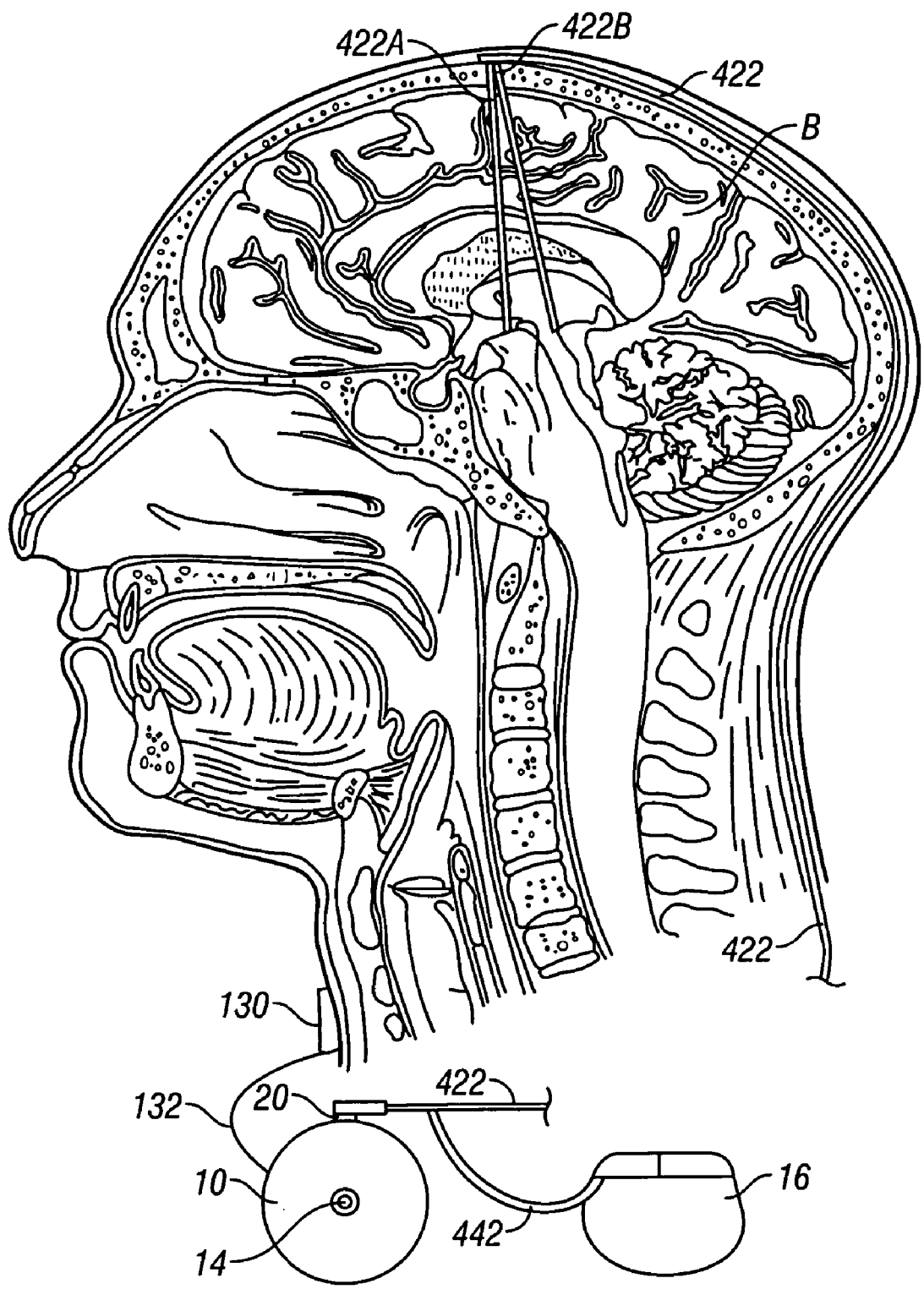
FIG. 4 is a diagrammatic illustration of a stuttering-treatment system in which a sensor is located near the patient's vocal folds and is used to control the amount of treatment delivered.

FIG. 4 shows the placement of a sensor, 130, near the vocal cords of a patient. The sensor 130 is coupled to the pump 10 via cable 132. The vocal cords produce electrical signals, such as electromyographic (EMG) and electroglottographic (EGG) signals, that can be detected and used to control the treatment method. For example, when a patient begins to speak, sensor 130 could detect the vocal-fold activity and send a signal to the treatment device to indicate that therapy should begin. In this embodiment, the treatment is delivered and continues to be delivered continuously as the patient speaks. Alternatively, the sensor could be coupled to a microprocessor that contains speech recognition software stored in memory. The speech recognition software could be programmed to distinguish between stuttering and normal speech by detecting a predetermined number of repetitions of a speech pattern. For example, treatment could begin upon detecting three repetitions of a particular speech pattern. The software could analyze an EMG or EGG waveform from the vocal folds, or signals from a microphone, either implanted or placed externally on a person's neck near the person's vocal folds.

Figure 13:
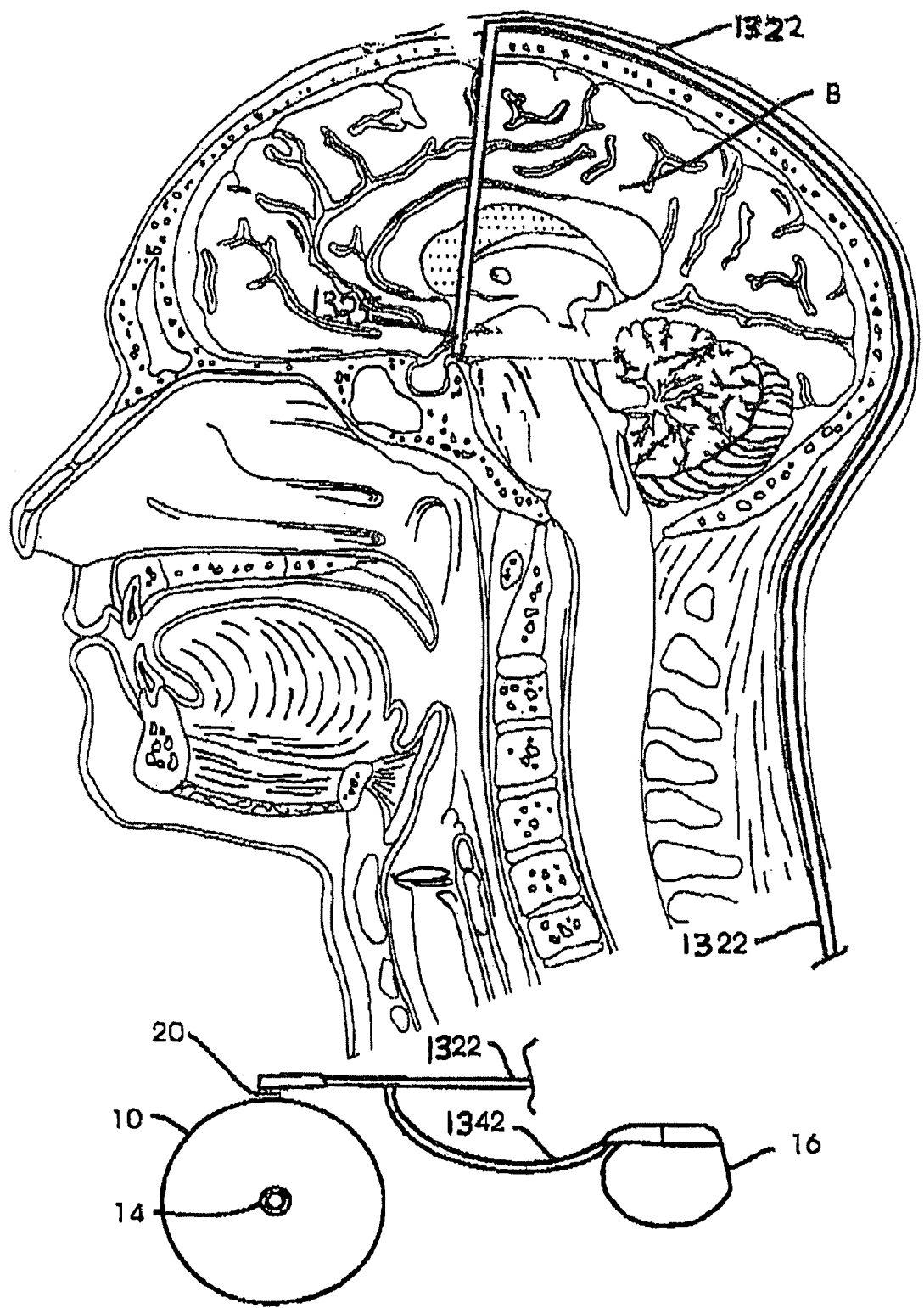
FIG. 13 is a diagrammatic illustration of a stuttering-treatment system in which a sensor is implanted in a patient's brain and is used to control the amount of treatment delivered.

FIG. 13 shows the placement of a sensor, 1325, located in a specific region of the brain to detect electroencephalogram (EEG) signals. The sensor 1325 may be coupled to the pump 10 and the signal generator 16 through the combined catheter electrode 1322. The EEG signals may be detected and analyzed for abnormal activity related to stuttering with the use of a microprocessor that contains EEG recognition software stored in memory. In this embodiment, treatment is delivered and may continue to be delivered based on the recorded electrical activity as seen by sensor 1325.

Several other techniques, which are well known in the art, could also be used in accordance with the invention for detecting speech disfluency. For instance, as described in more detail above, each of U.S. Pat. Nos. 4,020,567, 5,794,203, and 6,231,500, which are incorporated herein by reference, disclose speech-disfluency-detection devices that could be used with this invention.

Figure 5:
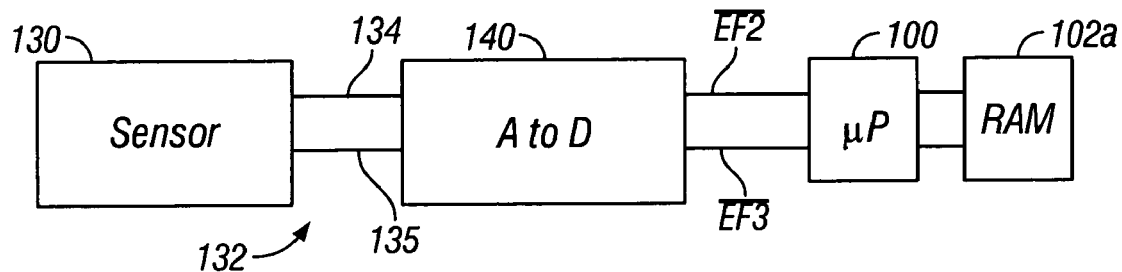
FIG. 5 is a schematic block diagram of a microprocessor and related circuitry for using the sensor to control drug delivery to the brain.

The amount and type of stimulation delivered in accordance with the invention may be controlled based upon analysis of the output from a sensor, such as sensor 130 shown in FIG. 4. Referring to FIG. 5, the output of a sensor 130, which could be an EEG, EMG or EGG sensor, micropower impulse radar, or a microphone as described above, is coupled by a cable 132 comprising conductors 134 and 135 to the input of analog to digital converter 140. Alternatively the output of the sensor 130 could communicate through a "body bus" communication system as described in U.S. Pat. No. 5,113,859 (Funke), which is assigned to Medtronic and which is incorporated herein by reference. Alternatively, the output of an external feedback sensor 130 would communicate with the implanted pulse generator 16 or pump 10 through a telemetry down-link. The output of the analog to digital converter 140 is connected to terminals EF2 BAR and EF3 BAR. Such a configuration may be one similar to that shown in U.S. Pat. No. 4,692,147 ("'147 Patent") except that before converter 140 is connected to the terminals, the demodulator of the '147 patent (identified by 101) would be disconnected. A drug can be delivered essentially continuously (within the constraints of the particular delivery device being used) or it may be delivered during intermittent intervals coordinated to reflect the half-life of the particular agent being infused or with circadian rhythms. As an example, stuttering will typically occur less frequently at night when the person is sleeping so the drug delivery rates might be reduced to coincide with the hours between 10 p.m. and 7 a.m.

Figure 6:
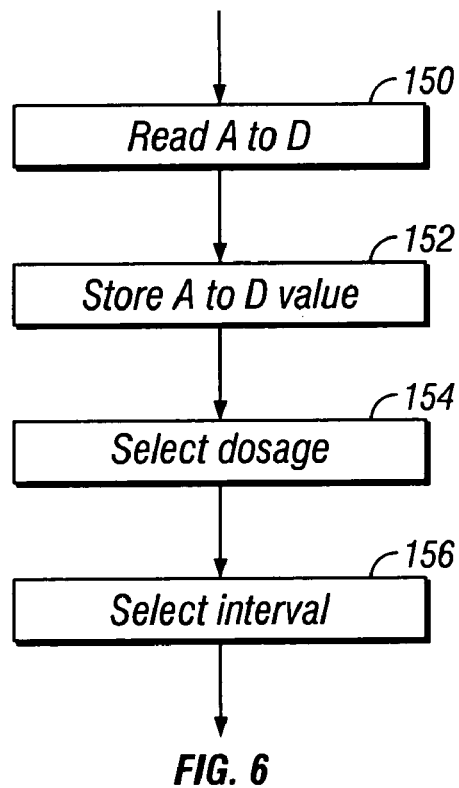
FIG. 6 is a flow chart illustrating a preferred form of a microprocessor program for using the sensor to control drug dosage administered to the brain.

An exemplary computer algorithm is shown in FIG. 6. Referring to FIGS. 5 and 6, microprocessor 100 included within pump 10 reads converter 140 in step 150, and stores one or more values in RAM 102a in step 152. A dosage is selected in step 154, and an appropriate time interval is selected in step 156. The selected dosage and interval of a drug is then delivered through catheter 222 and tube 222A to the basal ganglia of the brain as described in the '147 Patent.

For some types of sensors, a microprocessor and analog to digital converter will not be necessary. An appropriate elect filter can be used to filter the output from sensor 130 to provide a control signal for signal generator 16. An example of such a filter is found in U.S. Pat. No. 5,259,387 "Muscle Artifact Filter", Issued to Victor de Pinto on Nov. 9, 1993, incorporated herein by reference.

Figure 7:
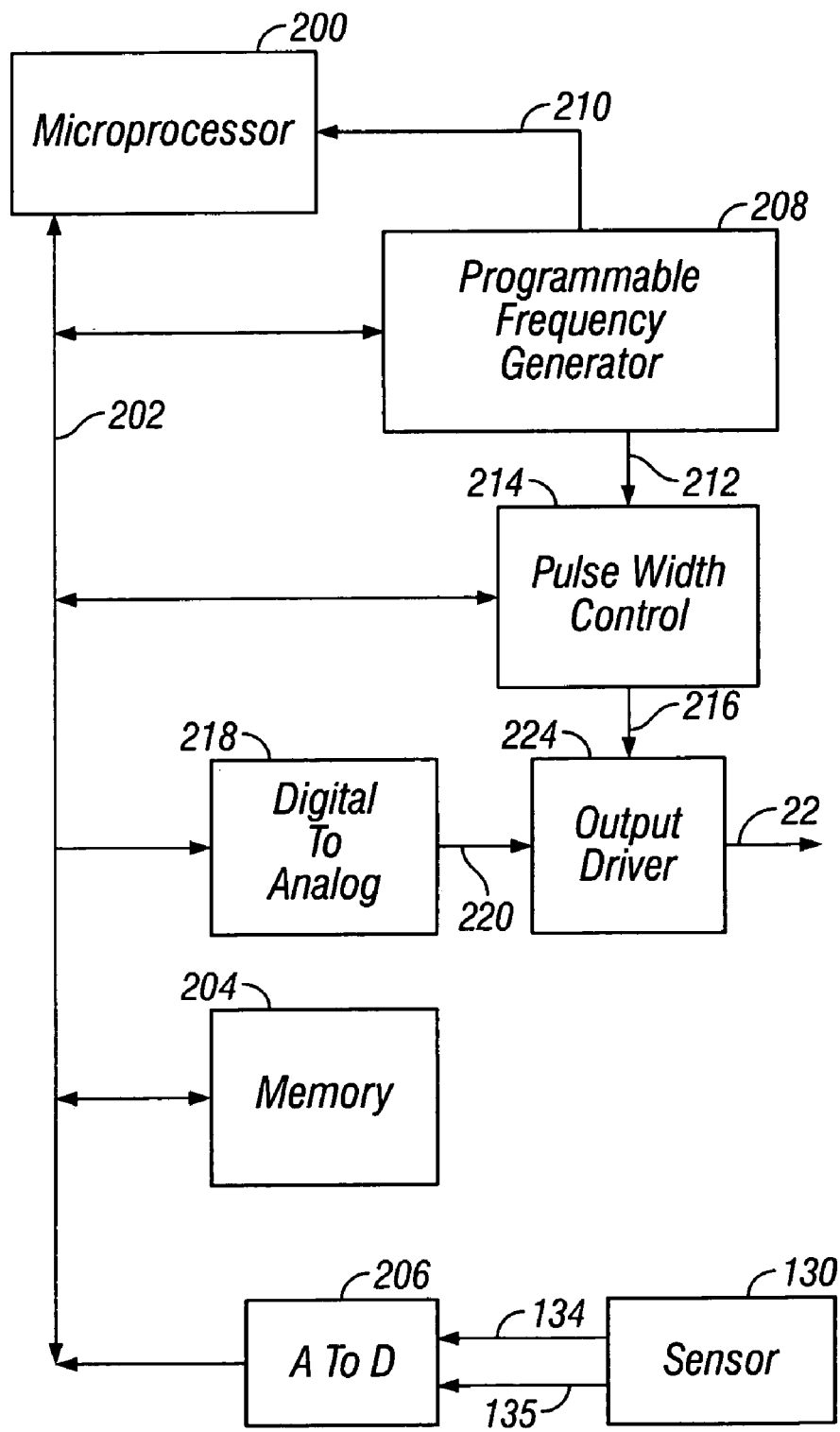
FIG. 7 is a schematic block diagram of a microprocessor and related circuitry for using the sensor to control electrical stimulation administered to the brain.

A modified form of the ITREL II® signal generator can be used to achieve closed-loop electrical stimulation, which is schematically depicted in FIG. 7. The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a sensor-signal threshold level stored in a memory 204, increasing amounts of stimulation will be applied through an output driver 224. The sensor-signal threshold level could be set such that the sensor signal will exceed the threshold whenever the person is speaking. Alternatively, increasing amounts of stimulation could be applied through the output driver 224 when speech-processing software detects a speech pattern that is likely to correspond to stuttering.

Programming a value to a programmable frequency generator 208, using bus 202, controls the stimulus pulse frequency. The programmable frequency generator provides an interrupt signal to microprocessor 200 through an interrupt line 210 when each stimulus pulse is to be generated. The frequency generator may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude. Microprocessor 200 also programs a pulse width control module 214 using bus 202. The pulse width control provides an enabling pulse of duration equal to the pulse width via a conductor. Pulses with the selected characteristics are then delivered from signal generator 16 through cable 22 and lead 22A to the target locations of a brain B.

Microprocessor 200 executes an algorithm shown in FIGS. 8-12 in order to provide stimulation with closed loop feedback control. At the time the stimulation signal generator 16 or alternative device in which the stimulation and infusion functions are combined is implanted, the clinician programs certain key parameters into the memory of the implanted device via telemetry. These parameters may be updated subsequently as needed. Step 400 in FIG. 8 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of release for pulse width (step 400(3)), amplitude (step 400(4)) and frequency (step 400(5)) which signal generator 16 may use to optimize the therapy. The clinician may also choose the order in which the parameter changes are made (step 400(6)). Alternatively, the clinician may elect to use default values.

Figure 8:
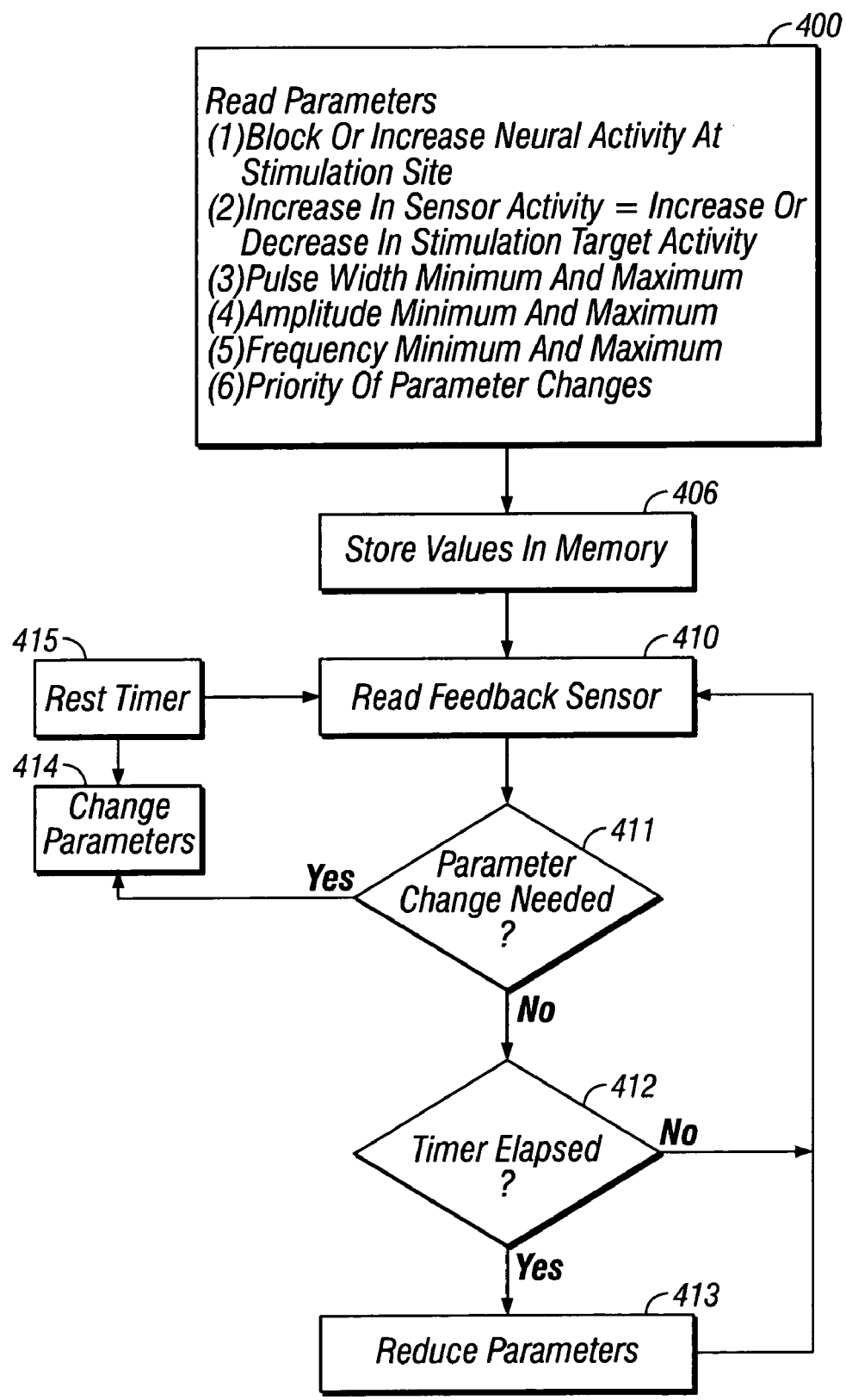
FIGS. 8-12 are flow charts illustrating a preferred form of a microprocessor program for generating electrical stimulation pulses to be administered to the brain.

The algorithm for selecting parameters is different depending on whether the clinician has chosen to block the neural activity at the stimulation target or facilitate the neural activity. FIG. 8 details steps of the algorithm to make parameter changes.

Figure 9:
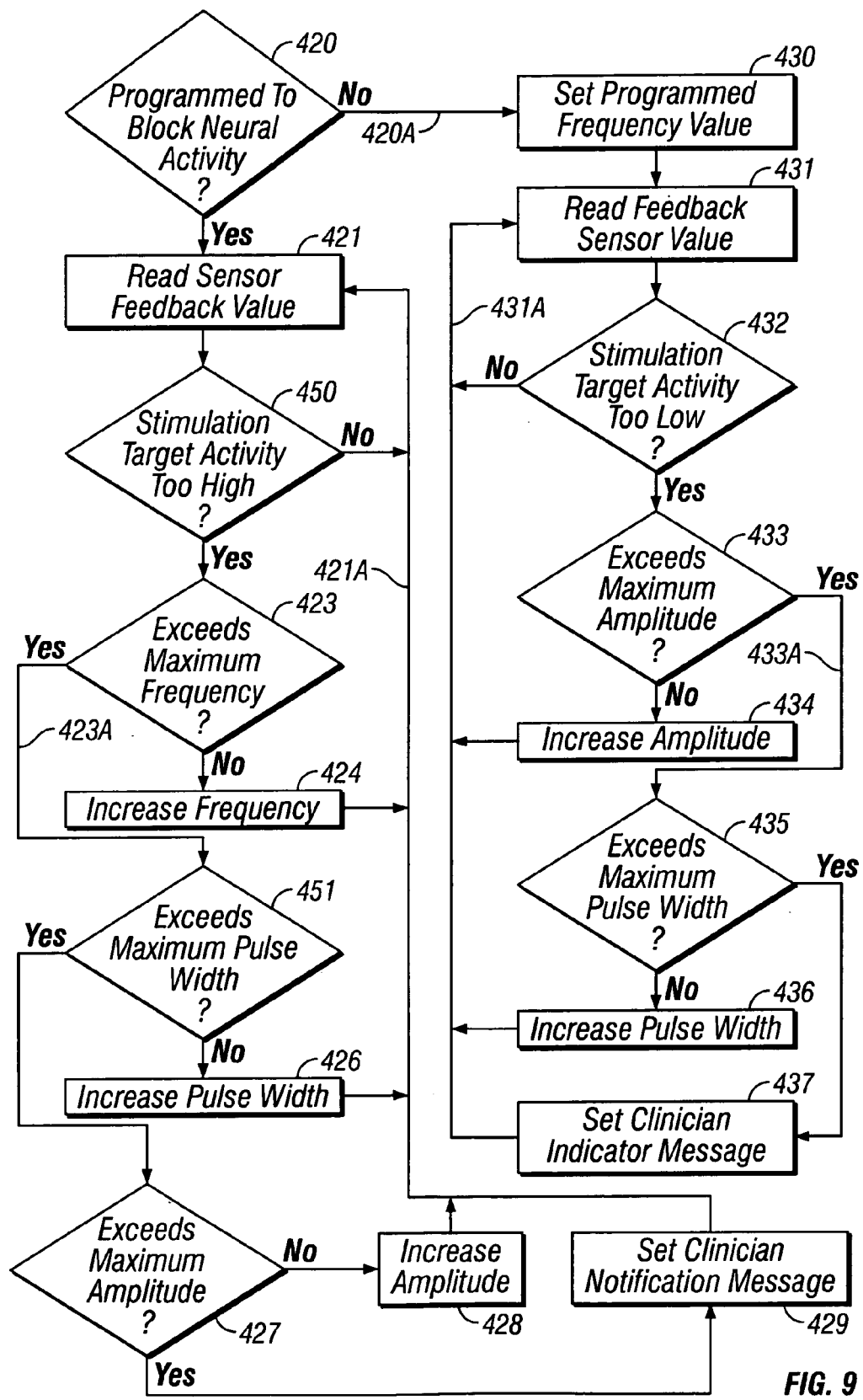
Figure 10:
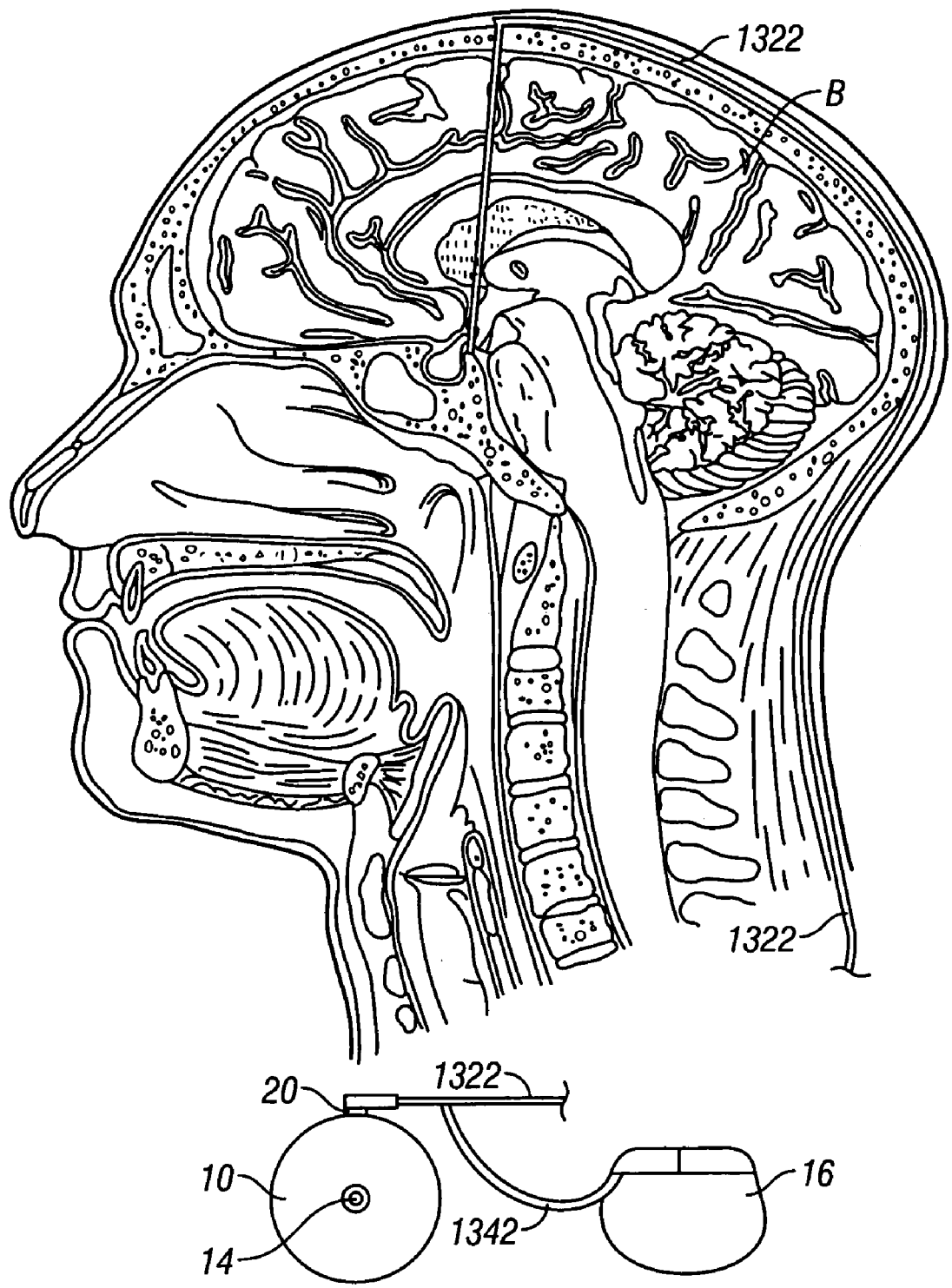
Figure 11:
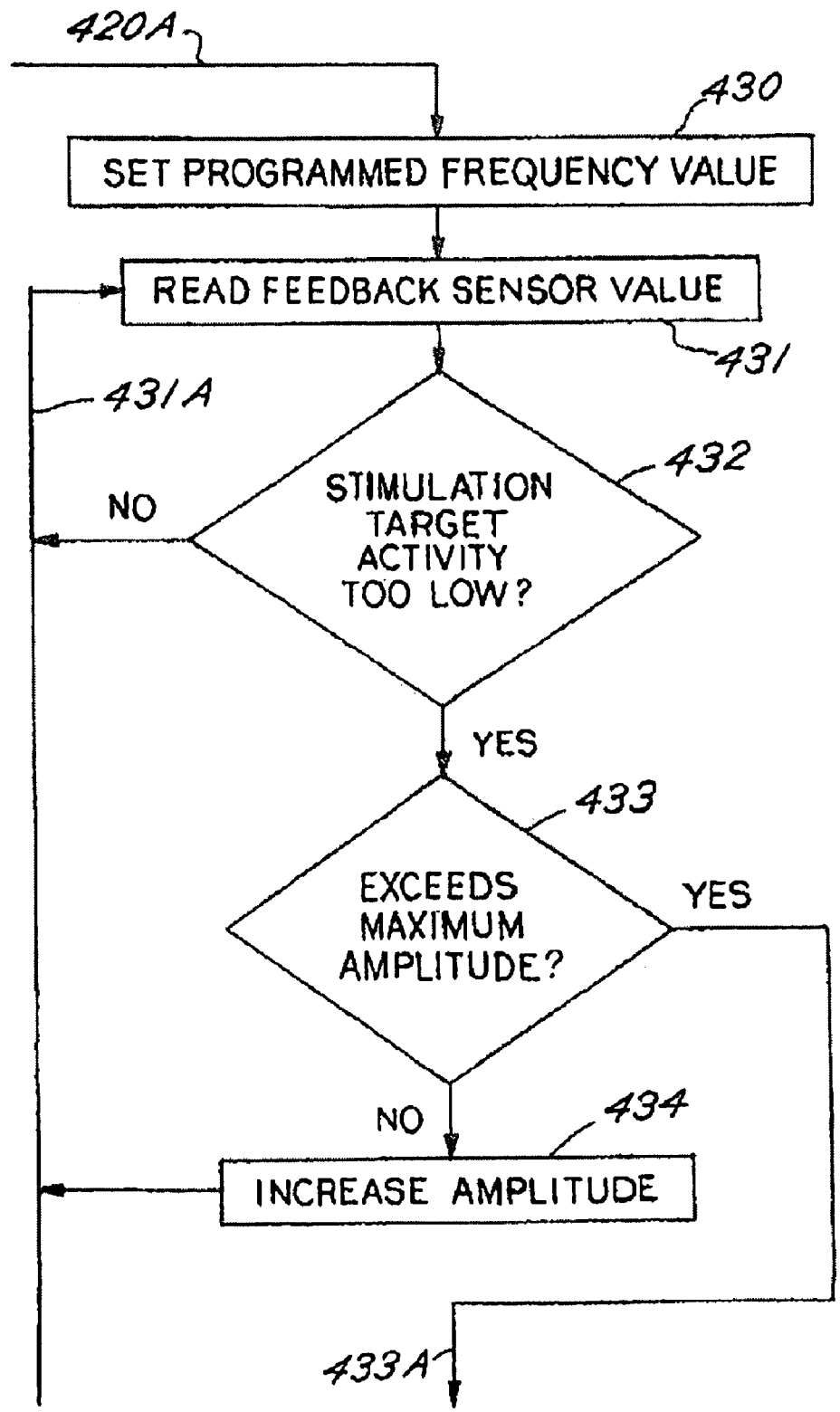

The algorithm uses the clinician programmed indication of whether the neurons at the particular location of the stimulating electrode are to be facilitated or blocked in order to decide which path of the parameter selection algorithm to follow (step 420, FIG. 9). If the neuronal activity is to be blocked, signal generator 16 first reads the feedback sensor 130 in step 421. If the sensor values indicate a likelihood that the activity in the neurons is too high (step 450), for instance, if speech processing software detects a speech pattern likely to correspond to stuttering, the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feedback signal from sensor 130.

If the frequency parameter is at the maximum, the algorithm next increases the pulse width in step 426 (FIG. 10), again with the condition that this parameter has not exceeded the maximum value as checked for in step 451 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 16 is unable to reduce neural activity to the desired level.

Figure 12:
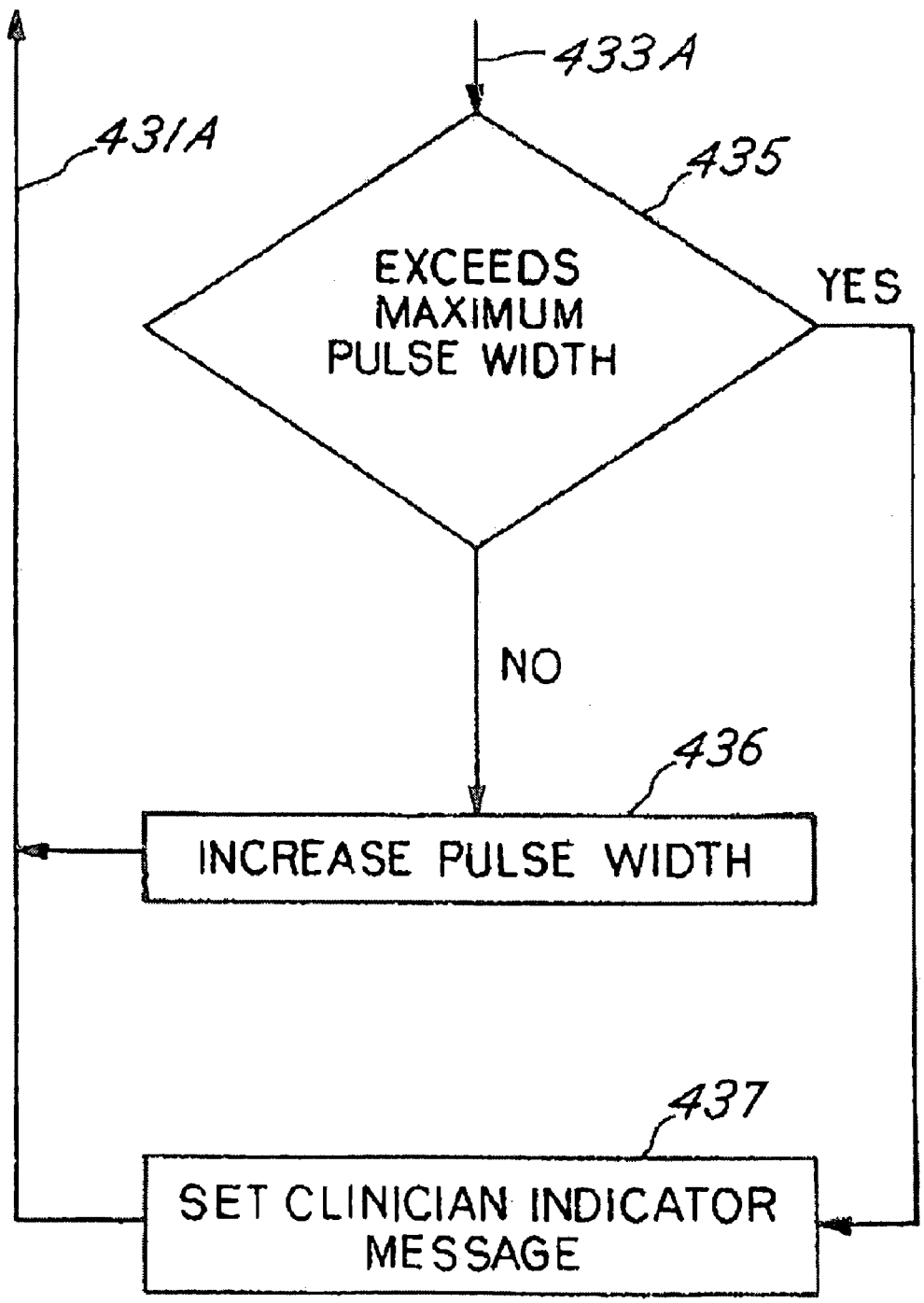

If, on the other hand, the stimulation electrode is placed in a location which the clinician would like to activate in order to alleviate stuttering, the algorithm would follow a different sequence of events. In the preferred embodiment, the frequency parameter would be fixed at a value chosen by the clinician to facilitate neuronal activity in step 430 (FIG. 11) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 12). A lack of adequate alteration of the symptoms of the neurological disorder, even though maximum parameters are used, is indicated to the clinician in step 437. After steps 434, 436 and 437, the algorithm returns to step 431 through path 431A, and the feedback sensor is read again.

It is desirable to reduce parameter values to the minimum level needed to establish the appropriate level of neuronal activity in, for example, the target brain nucleus. Superimposed on the algorithm just described is an additional algorithm to readjust all the parameter levels downward as far as possible. In FIG. 8, steps 410 through 415 constitute the method to do this. When parameters are changed, a time is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, signal generator 16 tries reducing a parameter in step 413 to determine if control is maintained. If it is, the various parameter values will be ratcheted down until such time as the sensor values again indicate a need to increase them. While the algorithms in FIGS. 8-12 follow the order of parameter selection indicated, other sequences may be programmed by the clinician.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims and their equivalents.

What is claimed is:

1. A method for therapeutically treating stuttering in a patient having a vocal fold, comprising:
   delivering a drug using a pump and at least one catheter having a proximal end coupled to the pump and having a discharge end adjacent to a predetermined site in the brain selected from a group consisting of the supplementary motor area, the centromedian circuit, the dorsomedial nuclei, the lateral prefrontal circuit, the red nucleus, the habenulointerpeduncular tract, the prerubral area, the zona incerta, the thalamic primary sensory relay nuclei, the parafasicular nucleus, and the intralaminar nucleus;
   generating a signal responsive to activity of the patient's speech-producing muscles using a sensor positioned near the vocal fold of the patient; and
   regulating dosage of the drug using a controller in response to the signal from the sensor to reduce activity, corresponding to stuttering, of the patient's speech-producing muscles.

2. The method of claim 1, wherein the sensor is an electromyographic sensor.

3. The method of claim 1, wherein the sensor is an electroglottographic sensor.

4. The method of claim 1, wherein the controller discharges the drug dosage at a first rate at times when the patient is expected to be awake, and at a second rate when the patient is expected to be asleep, the second rate being reduced relative to the first rate.

5. The method of claim 1, further comprising:
delivering electrical stimulation to at least one predetermined electrical stimulation site of the patient's brain using a signal generator and at least one implantable lead coupled to the signal generator.

6. The method of claim 5, further comprising using a controller to perform speech-recognition processing on the signal from the sensor to detect stuttering and to adjust at least one stimulation parameter of the electrical stimulation in response to detecting stuttering.

7. The method of claim 5, further comprising using a controller to detect when the patient starts speaking and to start the electrical stimulation in response to detecting that the patient has started to speak.

8. The method of claim 5, further comprising using a controller to stop the electrical stimulation a predetermined amount of time after the patient has started to speak.

9. A method for therapeutically treating stuttering in a patient having a vocal fold comprising:
delivering a drug using a pump and at least one catheter having a proximal end coupled to the pump and having a discharge end adjacent to a predetermined site in the brain selected from a group consisting of the supplementary motor area, the centromedian circuit, the dorsomedial nuclei, the lateral prefrontal circuit, the red nucleus, the habenulointerpeduncular tract, the prerubral area, the zona incerta, the thalamic primary sensory relay nuclei, the parafasicular nucleus, and the intralaminar nucleus;
generating a signal indicative of speech-producing muscle activity of the patient using a sensor positioned near the vocal fold of the patient; and
regulating dosage of the drug using a controller responsive to the signal from the sensor to reduce activity, corresponding to stuttering, of the patient's speech-producing muscles.

10. A method for therapeutically treating stuttering in a patient comprising:
delivering at least one drug using a pump and at least one catheter having a proximal end coupled to the pump and having a discharge end adjacent to a predetermined drug delivery site in the brain selected from a group consisting of the supplementary motor area, the centromedian circuit, the dorsomedial nuclei, the lateral prefrontal circuit, the red nucleus, the habenulointerpeduncular tract, the prerubral area, the zona incerta, the thalamic primary sensory relay nuclei, the parafasicular nucleus, and the intralaminar nucleus;
regulating drug dosage using a controller responsive to circadian rhythms to reduce stuttering, wherein the regulating comprises:
discharging the at least one drug to the predetermined site at a first rate at times when the patient is expected to be awake, and
discharging the at least one drug to the predetermined site at a second rate when the patient is expected to be asleep, the second rate being reduced relative to the first rate.

11. The method of claim 10 further comprising:
delivering electrical stimulation to at least one predetermined electrical stimulation site of the patient's brain using a signal generator and at least one implantable lead coupled to the signal generator.

12. The method of claim 11 further comprising:
using a sensor, generating a signal indicative of activity of the patient's speech-producing muscles; and
using a controller that performs speech-recognition processing on the signal from the sensor to detect stuttering and to adjust at least one stimulation parameter of the electrical stimulation in response to detecting stuttering.

13. The method of claim 12, wherein the sensor is an electromyographic sensor.

14. The method of claim 12, wherein the sensor is an electroglottographic sensor.

15. The method of claim 12, further comprising detecting, by the controller, when the patient starts speaking and starting the electrical stimulation in response to detecting that the patient has started to speak.

16. The method of claim 15, further comprising stopping, by the controller, the electrical stimulation a predetermined amount of time after the patient has started to speak.

17. The method of claim 11 further comprising:
generating a signal responsive to activity of the patient's speech-producing muscles using a sensor; and
using a controller that includes a speech-recognition module, performing speech-recognition processing on the signal from the sensor to detect stuttering and to adjust at least one stimulation parameter in response to detecting stuttering.

18. The method of claim 17, wherein the sensor is a microphone.

19. The method of claim 18, wherein the microphone is human-implantable.

20. The method of claim 17, wherein performing the speech-recognition processing to detect stuttering further comprises detecting a predetermined number of repetitions of a speech pattern.

21. A method for therapeutically treating stuttering in a patient having a vocal fold comprising:
delivering a drug using a pump and at least one catheter having a proximal end coupled to the pump and a discharge end adjacent to a predetermined drug delivery site in the brain selected from a group consisting of the supplementary motor area, the centromedian circuit, the dorsomedial nuclei, the lateral prefrontal circuit, the red nucleus, the habenulointerpeduncular tract, the prerubral area, the zona incerta, the thalamic primary sensory relay nuclei, the parafasicular nucleus, and the intralaminar nucleus;
delivering electrical stimulation to at least one predetermined electrical stimulation site of the patient's brain using a signal generator and at least one implantable lead coupled to the signal generator;
generating a signal indicative of activity of the patient's speech-producing muscles using a sensor located in proximity to the vocal fold of the patient; and
using a controller to adjust at least one stimulation parameter of the electrical stimulation in response to the signal.

22. The method of claim 21 wherein the controller includes a speech-recognition module for performing speech-recognition processing on the signal from the sensor to detect stuttering and to adjust at least one stimulation parameter in response to detecting stuttering.

23. The method of claim 21, wherein the controller detects when the patient starts speaking and starts the electrical stimulation in response to detecting that the patient has started to speak.

24. The of claim 23, wherein the controller stops the electrical stimulation a predetermined amount of time after the patient has started to speak.

25. The method of claim 21, wherein the sensor is an electromyographic sensor.

26. The method of claim 21, wherein the sensor is an electroglottographic sensor.

27. The method of claim 21, wherein the sensor is a microphone.

28. The method of claim 27, wherein the microphone is human-implantable.

* * * * *